United States Patent
Vogtmeier

(10) Patent No.: US 8,767,909 B2
(45) Date of Patent: Jul. 1, 2014

(54) C-ARM X-RAY SYSTEM

(75) Inventor: Gereon Vogtmeier, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 340 days.

(21) Appl. No.: 13/139,393

(22) PCT Filed: Dec. 11, 2009

(86) PCT No.: PCT/IB2009/055684
§ 371 (c)(1),
(2), (4) Date: Jun. 13, 2011

(87) PCT Pub. No.: WO2010/070560
PCT Pub. Date: Jun. 24, 2010

(65) Prior Publication Data
US 2011/0243303 A1    Oct. 6, 2011

(30) Foreign Application Priority Data
Dec. 18, 2008    (EP) .................................. 08172139

(51) Int. Cl.
*A61B 6/00*    (2006.01)
(52) U.S. Cl.
USPC ............................................. 378/9; 378/193
(58) Field of Classification Search
USPC ................................... 378/9, 92, 193
See application file for complete search history.

(56) References Cited

U.S. PATENT DOCUMENTS

| | | | |
|---|---|---|---|
| 7,453,976 B1 * | 11/2008 | Yin | 378/9 |
| 2004/0057552 A1 | 3/2004 | Collins et al. | |
| 2004/0066907 A1 | 4/2004 | Fadler | |
| 2004/0213378 A1 | 10/2004 | Zhou et al. | |
| 2006/0050847 A1 | 3/2006 | Jaffray et al. | |
| 2007/0098136 A1 | 5/2007 | Lutz | |
| 2007/0133747 A1 | 6/2007 | Manak et al. | |

FOREIGN PATENT DOCUMENTS

| | | |
|---|---|---|
| DE | 102005052131 A1 | 10/2005 |
| WO | 2006090323 A2 | 8/2006 |
| WO | 2009101576 A1 | 8/2009 |

OTHER PUBLICATIONS

G Z Yue et al: "Generation of Continuous and Pulsed Diagnostic Imaging X-Ray Radiation Using a Carbon-Nanotube-Based Field-Emission Cathode" Applied Physics Letters, AIP, American Institute of Physics, Melville, NY, US, vol. 81, No. 2, Jul. 8, 2002, pp. 355-357, XP012032476 ISSN: 0003-6951 the whole document.

* cited by examiner

*Primary Examiner* — Jurie Yun

(57) ABSTRACT

The c-arm x-ray system according to the present invention presents a system that provides at least one x-ray beam projection and an auxiliary projection without the need to rearranging or move elements of the c-arm to avoid inaccuracies through mechanical deflection of the supporting c-arm. This is achieved by comprising a main x-ray source, and at least one auxiliary x-ray source with a lower continuously radiated power than the main x-ray source and mechanically coupled to the main x-ray source, which is formed as a cold carbon nanotube based field emitter.

16 Claims, 2 Drawing Sheets

C-ARM X-RAY SYSTEM

FIELD OF THE INVENTION

The present invention relates to the field of c-arm x-ray systems and in particular a support for a main x-ray source and at least one auxiliary x-ray source, which provides additional available x-ray beams for multi-planar image mapping, which are detected and processed to achieve additional projection image information without shifting the position of the c-arm.

BACKGROUND OF THE INVENTION

X-ray technology is widely used for medical, industrial and security imagining purposes. The designs of current c-arm x-ray machines for medical purposes with conventional x-ray imaging exposures a three-dimensional object to form a two-dimensional image. As a result, the 3D spatial resolution in the projection direction is lost. This limitation can be overcome by using c-arm systems and moving the c-arm into different positions to obtain images of the object of interest from different points of view with the so called multi-planar mapping.

Particularly the cardiovascular surgery poses high demanding requirements on the x-ray systems. Additional information of different projections is very important during planning and execution of cardiovascular surgery or catheter manipulation. In prior art this could be achieved by volume imaging methods utilizing a c-arm.

In detail, for the purpose of volume imaging with a current c-arm device, the source and the detector of the c-arm rotates more than 180 degrees on a circular trajectory around the object of interest, e.g. a patient, or to obtain 3D spatial depth information. Several successive mapping images of the object are obtained to achieve the data for constructing of a full three dimensional dataset of the scanned volume. The c-arm carries the radiation source and the detector, both of which are of physically heavy weight in current embodiments. During the rotation of the c-arm on a semi circular trajectory the weight force on both of the devices act perpendicular, whereby the burden on the c-arm throughout the acting of weight forces changes with the rotation of the c-arm, and whereby this results in mechanical deformation of the c-arm construction. For example, if the rotation of the c-arm starting at a horizontal position and the c-arm is turning over 180 degrees into reverse horizontal position, the weight forces acting at the ends of the c-arm cause the maximal mechanical deflection of the c-arm, due to the weight of the detector and the x-ray tube. In consequence the deformation induces a rotation-dependent variation of the alignment of the detector and the radiation source, though that the detector and the radiation source are not arranged opposite to each other. This drawback of the current c-arm construction accounts to the forming of artifacts in multi-planar mapping of the data of the object of interest.

The US Patent Application Number 2004/066907 A1 discloses a medical x-ray diagnostic installation that has a first x-ray radiator attached to a c-arm as well as a second x-ray radiator that is mounted separately from the c-arm at a holder device that can be attached to a stationary structure. A radiation receiver that optionally detects the x-rays emitted by the first x-ray radiator or the x-rays emitted by the second x-ray radiator is attached to the c-arm. The radiation receiver can preferably be rotated around an axis that resides perpendicularly on the plane defined by the c-arm. With this x-ray diagnostic installation, standard examinations for conventional c-arm devices can be implemented and computer tomographic exposures can be generated upon employment of the second X-radiator.

The PCT Application WO2006/090323 discloses a computer tomography apparatus for examination of an object of interest, the computer tomography apparatus comprising a first electromagnetic radiation source adapted to emit electromagnetic radiation to an object of interest, a second electromagnetic radiation source adapted to emit electromagnetic radiation to the object of interest, at least one detecting device adapted to detect electromagnetic radiation generated by the first electromagnetic radiation source and by the second electromagnetic radiation source and scattered on the object of interest, and a determination unit adapted to determine structural information concerning the object of interest based on an analysis of detecting signals received from the at least one detecting device.

SUMMARY OF THE INVENTION

An object of the present invention is to provide a system that with at least one x-ray beam projection and an auxiliary projection without the need to rearranging or move elements of the c-arm avoid inaccuracies through mechanical deflection of the supporting c-arm.

This will be achieved by the features of the present claim 1 as a c-arm for an x-ray system comprising, a main x-ray source, coupling means to couple the c-arm to a support, at least one auxiliary x-ray source with a lower continuously radiated power than the main x-ray source and mechanically coupled to the main x-ray source.

The c-arm is equipped with fixture means to allow the c-arm to be supported by a mobile or stationary support device, which also allows moving the c-arm in elevation and turning the c-arm on a circular track and other directions in a doctor's surgery, intensive care unit (ICU) or the like.

A surprisingly advantage of the present invention is to achieve additional projections of the object of interest during the surgery in the operating theatre, which is highly necessary, for example, to provide detailed information about the arrangement of a catheter in a vessel. If a catheter is advancing parallel to the x-ray direction of the main projection beam, it is highly desirable to rapidly obtain multi-planar mapping from different points of view in order to achieve the 3D spatial imaging information of the advancing catheter. However, in practical application it is not desirable to move or rotate the c-arm in an operating theatre because of obstacles in form of hoses and tubes of the life support system and other devices, which are attached to the patient during surgery, which constrain the movement of the c-arm.

Further, the c-arm provides at least one x-ray source that is formed as fixed anode x-ray source, advantageous a cold cathode based x-ray tube, e.g. carbon nanotube based field emitter, which allows generating x-ray radiation with a limited need of space, power and local cooling, compared with conventional x-ray generators but with the advantage of fast on-off-switching capabilities at the same time. Several applications will come into the mind of the person with skill in the art, in the present invention for example short-term x-ray flashes generated with CNT allow the medical practitioner taking x-ray images from different positions. Additionally, the moving or rotating of the c-arm extends the time of the surgery and adherently augments the health risk for the patient during surgery. With the aid of multi-planar mapping even small differences in the intensity of the x-ray beam exposing the tissue can be recognized. Therefore, the necessity for the application of contrast agents can be reduced.

Furthermore at least two carbon nanotube based emitters form a carbon nanotube x-ray source matrix, which advantageous allows taking of 3 D spatial or semi-three dimensional images by temporarily switching very fast auxiliary carbon nanotube based X-ray sources on, additionally to or alternately with the main x-ray source, that allows the combined employment of the supply equipment for all kind of tubes, i.e. the high voltage power generator, etc.

Additionally, since the at least one auxiliary x-ray source is provided at a support together with the main x-ray source, and which is temporarily switched on additionally to or alternately with the main x-ray source, this allows the medical practitioner more flexibility e.g. during in mapping continuous occurrences in surgery. Further, another advantage in case of the c-arm is the possibility of keeping the c-arm in stationary position during the entire imaging process. The patient undergoes little or no stress, which could cause any erroneous indication of an abnormality like higher blood pressure, higher heart rate, or higher adrenaline levels.

Additionally, the c-arm for an x-ray system is provided, wherein the main x-ray source and at least one auxiliary x-ray source provided with different voltages. This allows taking of several images with different contrast, which advantageously allows displaying e.g. tissues and imaging of carcinosis.

Additionally further the main x-ray source and the at least one auxiliary x-ray source are provided to be connected to a common high voltage generator with switching means to distribute electrical power to the main x-ray source and the at least one auxiliary x-ray source. This advantageously allows to addition technical features without or with small technical effort and consequently with small additional costs.

Further the present invention provides a c-arm, wherein the cooling of the at least one auxiliary x-ray source is provided as the local cooling. The cooling of the at least one auxiliary x-ray source could be formed less expensive compared to the cooling of the main x-ray device. An alternative embodiment is provided with a cooling that is less unpretentious than an air or water cooling and would form sufficient cooling means for the auxiliary x-ray tubes.

Additionally further the present invention is embodied as an x-ray system with c-arm comprising: a main x-ray source, coupling means to arrange the c-arm to a support, at least one auxiliary x-ray source with a lower continuous power than the main x-ray source and mechanically coupled to the main x-ray source, and a detector.

And additionally further the x-ray system with c-arm provides that the path of rays from the main x-ray source and the at least one auxiliary x-rays are respectively directed to the detector, and by processing the x-ray images projected on the detector three-dimensional spatial information can be extracted. This advantageously allows combining the several images of the object of interest with suitable software to a 3D spatial projection image, which is temporarily switching on additionally to or alternately with the main x-ray source. In all cases of cardiovascular surgery the x-ray system allows a more detailed planning and implementation for the medical practitioner with less inconvenience for the patient than prior art imaging methods.

Additionally further, it is an object of the present invention to provide a method for obtaining a three dimensional image by realizing the emitting x-rays from multiple positions by keeping the overall stationary position of the c-arm and allowing a continuous access to the object of interest comprising the steps: providing a projection of the object of interest from the main x-ray source, providing a projection of the object of interest from the at least one auxiliary x-ray source, and generating 3D-spatial information of the object of interest from the first and at least the second path of rays projection image of the object of interest.

The method relating to the present invention allows the medical practitioner taking x-ray images from different view with high flexibility and taking of semi 3D images without mechanical turning the c-arm and allows saving the application of contrast fluids.

BRIEF DESCRIPTION OF THE DRAWINGS

The invention will be described in more detail hereinafter with reference to examples of embodiment but to which the invention is not limited.

DETAILED DESCRIPTION OF EMBODIMENTS

Figure 1:
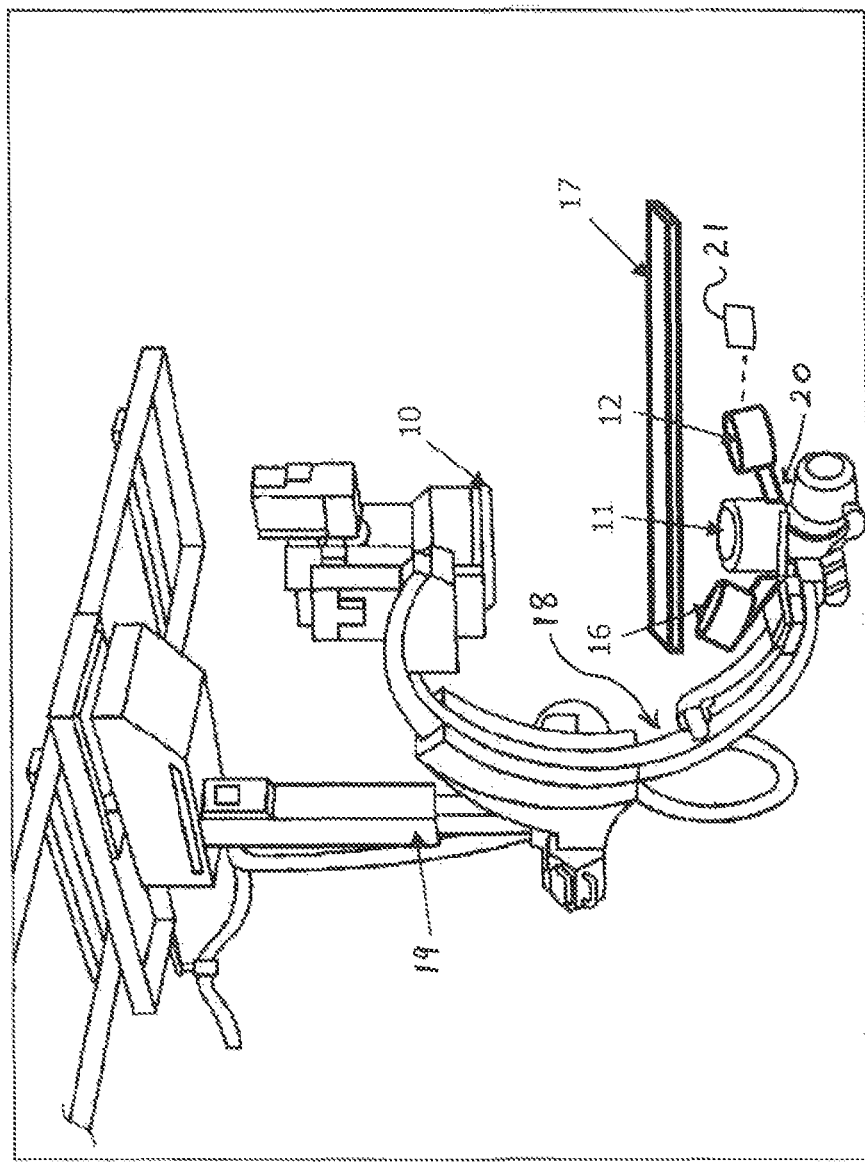
FIG. 1 shows a c-arm x-ray system according to a first embodiment of the invention.

The illustration of the present invention in the drawings is schematically. In different drawings, similar or identical elements are provided with the same reference signs.

In common the treatment risk of a surgery for the patient rises with the duration of the treatment. Thus, it is one major object to keep the necessary treatment time as short as possible. The medical imaging system should advantageously provide a multi-planar mapping of the object of interest. The multi-planar image mapping enriches the two-dimensional x-ray images with spatial information and thus facilitates the orientation during the positioning of a catheter, reduces the demand on contrast agent and reduces the residence time of the catheter in the vessel. At the same time a classification of stenosis in the vessel can be diminished with the use of a multi-planar image mapping.

As shown in FIG. 1, a c-arm 18, coupled to a support 19, is arranged at the patient's table 17, a detector 10 is arranged above the patient's table, and the main x-ray source 11 is placed underneath the patient's table. Auxiliary x-ray tubes 12, 16 are placed to the right and to the left next to the main x-ray tube 11. The c-arm 18 can be rotated in both horizontal and vertical azimuth, and as well in the elevation. In the preferred embodiment of the present invention an auxiliary support arm 20 provides the two auxiliary x-ray tubes 12, 16. The auxiliary tubes 12, 16 can be formed as small "boxes" on an auxiliary e.g. "C-shaped" arm or auxiliary support 20 next to the main tube 11. As an option more than two tubes can be placed and/or the position of these tubes can be varied on the support arm. As a further advanced embodiment the tubes can be formed as an x-ray emitter with a carbon nanotube based field emitter e.g. a carbon nanotube (CNT) based field emitter, which can replace the thermionic vacuum tube x-ray emitter as a source, wherein at least two carbon nanotubes are adjacently aligned in a column or row formed on the support 20, which will be described further below.

The auxiliary X-ray source could be a fixed anode X-ray source that has a carbon nanotube (CNT) based field emitter instead of a thermionic electron emitter. The carbon nanotubes are coated on a structured substrate to build together with the electrodes in front of the substrate an electron field emitter and placed in the x-ray tube on the place of the commonly used thermionic electron emitter. Advantage of such a field emitter is the fast switching capability and the option of structuring the substrate to form different emitter geometries or matrix structures out of several emitters.

In another embodiment, the c-arm system is mounted on a trolley stand and provides a mobile c-arm system. The mobile c-arm system provides the same features than the stationary mounted, but allows application in smaller surgeries or in emergency rooms.

The present invention provides a system for multi-planar mapping from different perspectives and viewing angles without the need of moving the c-arm. Instead, auxiliary x-ray tubes on the auxiliary support, next to the main x-ray tube send out short flashes of x-ray beams to the detector 10. The mechanical rotation of the c-arm is avoided. Hence, the deflection of the c-arm due to the dislocation through the weight force was exposed through the x-ray source and detector 10 does not occur.

Current x-ray tubes like the main x-ray tube of the system high-performance tubes, i.e. which are equipped with a rotation anode systems and/or fluid metal in order to realize a high performance during long time period of x-ray emitting operation with a thermionic electron emitter.

In addition the auxiliary x-ray tubes are either equipped with a rotation anode systems and/or fluid metal but those provide a CNT as electron emitter. The auxiliary x-ray tubes are not operated for long periods, but for short and temporary flashes. The demands on operational performance and endurance of the flashing x-ray tubes are lower than the demands to the continuously operating main x-ray tube, especially the requirements in particular in cooling and continuous output performance.

Hence, the auxiliary x-ray tubes 12, 16 are used for short and temporary x-ray projection performance as x-ray flashes, which allow making the tubes less complex and costly. In some cases i.e. the cold cathode tubes, the local cooling 21 of the surrounding air convection is sufficiently, in other cases an air or water cooling would be sufficient.

In yet another embodiment of the invention, each of the x-ray sources from the plurality of x-ray sources comprises a cold cathode x-ray source. Each individual x-ray source from the plurality of x-ray sources can comprise a cold cathode device that includes a single cathode and a single anode element. The cold cathode device may advantageously be used to reduce the size and weight of the x-ray source to facilitate miniaturization and/or to allow the inclusion of a higher number of x-ray sources in a given area.

In one particular embodiment at least one auxiliary x-ray source 12, 16 is located at the auxiliary support 20 next to the main x-ray source 11. The auxiliary support arm 20 is designed rotatable with the main x-ray source 11 as a fixed center point and providing the auxiliary x-ray tubes 12, 16. In a preferred embodiment, the auxiliary support arm 20 is equipped with a servo motor in or a handle order to allow the medical practitioner to automatically or manually turn the auxiliary support arm, which allows making a multi imaginary mapping of different positions in the horizontal plane. This simplifies the handling and allows for a flexible use of the c-arm 18. One or more auxiliary x-ray sources 12, 16 can be mounted on the support and it would be preferable to shift in the auxiliary x-ray sources position on the arm 18, in order to have multiple illuminations from different locations. Additionally, by using an x-ray source matrix it would be possible to map several projections and then to achieve a three-dimensional image of the object of interest.

In one further embodiment of the present invention the x-ray sources will be formed by a least one carbon nanotube. Also the use of a carbon nanotube matrix is possible.

In a further embodiment of the invention, the cold cathode x-ray source comprises carbon nanotubes (CNTs). The CNTs are good field emitters or so-called cold cathodes. Advantages of using cold cathodes include lower power consumption, greater robustness and faster switch on in comparison to thermionic electron sources.

Cold cathodes give additional advantages, i.e. higher resolution, faster pulsed operation, and instant-on behavior. Cooling requirements are less stringent which results in lower set-up and operation costs and freedom of design. An important advantage of using cold cathodes is that instant emission of x-rays is possible, with the x-ray emission beginning the instant an extraction field is applied between the cold cathode and a target anode in the x-ray source. This facilitates faster imaging. Other advantages of using cold cathode x-ray sources include potential miniaturization of the imaging apparatus.

With the extension of multiple CNTs or CNT arrays a projection under several different projection angles can be achieved and this allows the acquiring of spatial images, i.e. 3D or semi 3D information mapping.

In another embodiment the at least one additional CNT X-ray tube is driven with a voltage, that has a different level than the main tube. This provides a multi energy imaging during scanning, with different features (e.g. contrasts) of pictures, taken by the different x-ray tubes.

In a further embodiment of the invention, the at least one auxiliary x-ray source 12, 16 is arranged to make a projection of an object at rest, when the imaging apparatus is in operation wherein the detector 10 is positioned to receive x-rays from at least one x-ray source 12, 16. An advantage of the embodied arrangement is, that with the c-arm arranged to be at rest, mechanical issues associated with design of the imaging apparatus are reduced. Furthermore, a stationary imaging setup facilitates the elimination of artifacts that are attributed to movement or rotation of either the imaging apparatus or the patient. As will be appreciated by a person skilled in the art, the generation of 3D images is simplified.

Figure 2:
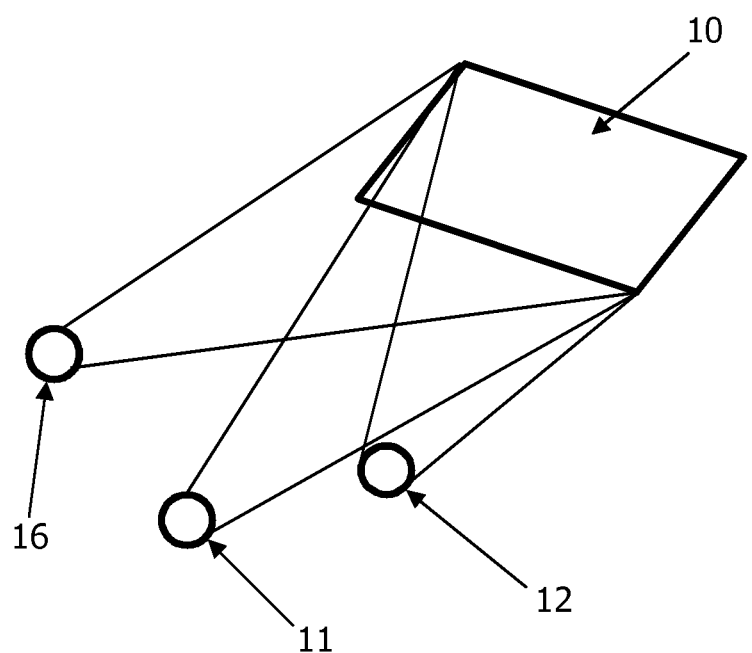
FIG. 2 shows a schematic drawing of a support of a c-arm x-ray system according to an embodiment of the invention.

FIG. 2 shows a schematic overview of the preferred embodiment of present invention. In this case there is a first x-ray source 11, and auxiliary x-ray sources 12, 16. The x-ray beams going out from the respective x-ray sources and the detector 10 are schematically depicted.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A c-arm for an x-ray system, said system including a support, said c-arm for coupling to said support, said c-arm comprising:

an x-ray source dedicated as a main x-ray source; and at least one x-ray source dedicated as an auxiliary x-ray source in that said auxiliary x-ray source is designed such that its outputted x-ray beam has a lower continuously radiated power than that of the main x-ray source, said auxiliary x-ray source being mechanically coupled to the main x-ray source.

2. A c-arm according to claim 1, wherein a source from among said at least one x-ray source is realized with a carbon nanotube based field emitter.

3. A c-arm according to claim 1, wherein said at least one x-ray source amounts to at least two x-ray sources that collectively form a carbon nanotube matrix, thereby allowing switching of said sources on, additionally to or alternately with the main x-ray source for acquiring three-dimensional or semi-three-dimensional images.

4. The x-ray system of claim 1, said system comprising said c-arm, the at least one auxiliary x-ray source, together with the main x-ray source, being provided together at said support, said system being configured for temporarily switching on a source from among said at least one auxiliary x-ray source additionally to or alternately with the main x-ray source.

5. The x-ray system of claim 1, said system comprising said c-arm, said system further comprising a switching configuration for connection to the main x-ray source and the at least one auxiliary x-ray source to distribute electrical power to the main x-ray source and the at least one auxiliary x-ray source.

6. A c-arm according to claim 1, wherein the main x-ray source is provided with a voltage that differs from that provided to a source from among the at least one auxiliary x-ray source.

7. A c-arm according to claim 1, wherein cooling of a source from among the at least one auxiliary x-ray source is provided locally as compared to cooling of the main x-ray source.

8. The x-ray system of claim 1, said system comprising said c-arm and a detector.

9. The x-ray system according to claim 8, configured with respective x-ray paths to said detector for said main x-ray source and a source from among said at least one x-ray source, said system being further configured for processing x-ray images projected, via correspondingly both paths, onto the detector and for extracting, from the projections, three-dimensional (3D)-spatial information.

10. The c-arm of claim 1, comprising at least two of said auxiliary x-ray sources, one of the at least two being disposed on one side of the main x-ray source, another of the at least two being disposed on an opposite side of the main x-ray source.

11. The c-arm of claim 1, comprising a transversely extending auxiliary support arm for supporting said at least one auxiliary x-ray source.

12. The c-arm of claim 1, said support being rotatable, said c-arm comprising a separately rotatable auxiliary support arm for supporting said at least one auxiliary x-ray source.

13. A method for obtaining a three dimensional image of an object of interest comprising the steps:
using a dedicated main x-ray source to make a projection of the object of interest;
to make respective projections of the object of interest, using at least one x-ray source dedicated as an auxiliary x-ray source in that said auxiliary x-ray source is designed such that its outputted x-ray beam has a lower continuously radiated power than that of the main x-ray source, said at least one x-ray source being mechanically coupled to the main x-ray source so as to realize a c-arm that includes said main x-ray source and said at least one x-ray source;
emitting x-rays from multiple positions while keeping an overall stationary position of said c-arm and while allowing continuous access to said object of interest; and
generating three-dimensional (3D)-spatial image information of the object of interest from collectively said projection and one or more of said respective projections.

14. The method of claim 13, further comprising:
after the making of said projection and said respective projections, rotating in unison, to new respective orientations, the dedicated main source and the dedicated at least one auxiliary source, via said c-arm; and
at said new respective orientations, remaking, for said object of interest via said dedicated sources, said projection and said respective projections and generating, from the remade projections and respective projections, new 3D-spatial image information.

15. A non-transitory computer readable medium embodying a program for obtaining a three dimensional image of an object of interest, said program having instructions executable by a processor for performing a plurality of acts, among said plurality being the acts of:
using a dedicated main x-ray source to make a projection of the object of interest;
to make respective projections of the object of interest, using at least one x-ray source dedicated as an auxiliary x-ray source in that said auxiliary x-ray source is designed such that its outputted x-ray beam has a lower continuously radiated power than that of the main x-ray source, said at least one x-ray source being mechanically coupled to the main x-ray source so as to realize a c-arm that includes said main x-ray source and said at least one x-ray source;
emitting x-rays from multiple positions while keeping an overall stationary position of said c-arm and while allowing continuous access to said object of interest; and
generating three-dimensional (3D)-spatial image information of the object of interest from collectively said projection and one or more of said respective projections.

16. The computer readable medium of claim 15, among said plurality further being the acts of:
after the making of said projection and said respective projections, rotating in unison, to new respective orientations, the dedicated main source and the dedicated at least one auxiliary source, via said c-arm; and
at said new respective orientations, remaking, for said object of interest via said dedicated sources, said projection and said respective projections and generating, from the remade projection and respective projections, new 3D-spatial image information.

* * * * *